US00PP14626P29

(12) United States Plant Patent
Zerr

(10) Patent No.: US PP14,626 P2
(45) Date of Patent: Mar. 23, 2004

(54) POINSETTIA PLANT NAMED 'FISWHITE SILVER'

(50) Latin Name: *Euphorbia pulcherrima*
Varietal Denomination: Fiswhite Silver

(75) Inventor: Katharina Zerr, Höhr-Grenzhausen (DE)

(73) Assignee: Florfis AG (CH)

( * ) Notice: Subject to any disclaimer, the term of this patent is extended or adjusted under 35 U.S.C. 154(b) by 0 days.

(21) Appl. No.: 10/382,660

(22) Filed: Mar. 7, 2003

(51) Int. Cl.[7] ..... A01H 5/00
(52) U.S. Cl. ..... Plt./304
(58) Field of Search ..... Plt./304, 303

*Primary Examiner*—Bruce R. Campell
*Assistant Examiner*—June Hwu
(74) *Attorney, Agent, or Firm*—Foley & Lardner

(57) ABSTRACT

A new and distinct Poinsettia plant named 'Fiswhite Silver', characterized as having creamy-white bract color; medium to large size inflorescences with ovate bracts; light green to grayish green foliage with narrow, irregular white margins; just under medium sized, tight and bushy plant habit; and medium (mid season) flowering response.

1 Drawing Sheet

Latin name of the genus and species of the plant claimed: *Euphorbia pulcherrima* Willd. ex Klotzsch.
Variety denomination: Fiswhite Silver.

BACKGROUND OF THE INVENTION

The present invention relates to a new and distinct cultivar of poinsettia plant known by the cultivar name 'Fiswhite Silver', and botanically known as *Euphorbia pulcherrima.*

'Fiswhite Silver' was derived from a naturally occurring mutation in the variety 'Fispue White' (U.S. Plant patent application Ser. No. 08/099,764). The mutation was discovered by the inventor, Katharina Zerr, in a greenhouse in Hillscheid, Germany, in the winter of 1999/2000. Among a group of flowering plants of the parent variety one plant partly developing variegated foliage was found. These mutated branches were used for asexual propagation in the spring of 2000. The resulting plants appeared uniform, and the variegation of the leaves was stable. This result was confirmed when the propagation and examination was repeated on a larger scale in the fall of 2001.

Horticultural examination of the clone starting in 2000 and continuing thereafter has demonstrated that the combination of characteristics as herein disclosed for 'Fiswhite Silver' are firmly fixed and retained through successive generations of asexual reproduction.

BRIEF SUMMARY OF THE INVENTION

The following traits have been repeatedly observed and are determined to be basic characteristics of 'Fiswhite Silver', which in combination distinguish this Poinsettia as a new and distinct cultivar:

1. Creamy-white bract color;
2. medium to large size inflorescences with ovate bracts;
3. light green to grayish green foliage with narrow, irregular white margins;
4. just under medium sized, tight and bushy plant habit; and
5. medium (mid season) flowering response.

'Fiswhite Silver' has not been observed under all possible environmental conditions. The phenotype may vary significantly with variations in environment such as temperature, light intensity, and daylength. The following observations, measurements and comparisons describe plants grown in Hillscheid, Germany, under greenhouse conditions which approximate those generally used in commercial practice.

Of the may commercial cultivars known to the inventor, the most similar in comparison to 'Fiswhite Silver' is the parent cultivar 'Fispue White', and the related variety 'Fispue Silver', (U.S. Plant patent application Ser. No. 09/099,768, later withdrawn).

'Fispue White' is characterized by white colored bracts, medium-green foliage almost without lobes, upright, moderately tall plant habit and early beginning of flowering. In contrast to the uniform, medium-green leaves of 'Fispue White', 'Fiswhite Silver' has variegated foliage of lighter green color and with narrow white margins. 'Fiswhite Silver' has an intermediate plant size and growth habit between 'Fispue White' and 'Fispue Silver'.

In comparison to 'Fispue Silver', 'Fiswhite Silver' has a somewhat taller plant habit and wider bracts and leaves. Its variegated foliage is more regularly/uniform shaped, and deformations of edges occur to a distinctly lesser degree than with leaves of 'Fispue Silver'. Furthermore, 'Fiswhite Silver' is marketable about one week earlier than 'Fispue Silver', which is partly due to its larger bracts.

BRIEF DESCRIPTION OF THE DRAWING

The accompanying color photographic drawing shows typical inflorescence and foliage of 'Fiswhite Silver', with colors being as true as possible with illustrations of this type. The photograph shows a mature potted plant.

DETAILED BOTANICAL DESCRIPTION

The plants described were grown in a greenhouse in Hillscheid, Germany, in the fall of 2002. Rooted cuttings were planted into 14 cm pots on July 25, and were pinched on August 8, leaving 7–8 leaves. Initially, the temperature was between a minimum of 19° C. and 24.5° C. maximum (ventilation temperature), and lower beginning October 1, minimum 16° C. to 23° C. The plants initiated flowers under short-day conditions under natural short-day conditions in fall, no black cloth was applied.

Observations and measurements were mainly taken in mid December, when the plants were in full flower and about 20 weeks old.

In the following description color references are made to The Royal Horticultural Society Colour Chart (R.H.S.). The color values were determined indoors in a north light.

Plant:

*Form.*—Shrub, self-branching.

*Plant habit.*—Just under medium-sized and well-branched; pinched plants have a tight structure and are uniformly rounded, shape is almost perfectly semi-spherically when given sufficient space.

*Height* (*above soil line*).—23.5 cm.

*Width.*—43.4 cm.

*Average number of branches.*—7.0.

*Average length of branches.*—18–22 cm, diameter approximately 5 mm.

*Average number of inflorescence.*—6.4.

*Stem color.*—Green, RHS 143 A to 143 B, no anthocyanin.

*Internode length.*—About 15 mm.

*Rooting.*—Medium, sufficiently rooted for transplanting after about 24 days in a greenhouse at a temperature of 22–24° C.

*Blooming habit.*—Begin under natural short day conditions in fall; botanically (cyathia open) around December 1, commercially (bracts colored) marketable around December 1.

*Flowering response time.*—About 9.5 weeks.

Foliage:

*Shape.*—Ovate with rounded to obtuse base, very weak lobes and accuminate tip.

*Margin.*—Mostly entire, single notches may occur.

*Texture.*—Upper surface almost flat to slightly folded, weakly rugose, only weakly veined, Lower surface: flat and smooth, except for the slightly protruding midrib and finer side veins in a pinnate pattern.

*Vein coloration.*—Upper leaf surface vein color mainly pale green, RHS 145 B; lower leaf surface vein color is pale light green, RHS 145 C.

*Leaf blade size.*—Length 12.5 cm; width 7.8 cm.

*Petiole.*—Length about 5–6 cm, diameter 2.5–3 mm.

*Quantity.*—About 45 leaves per plant.

*Color.*—Generally light-green, slightly marbled near margin, additionally narrow, irregular white margin. Mature foliage: Upper surface main color RHS 139 C, small, grey-green areas near the margin RHS 194 A, white margin RHS 155 D; under surface, RHS 139 C, margin RHS 150 D. New foliage: Upper side main color closest to RHS 143 C; under side RHS 139 C.

*Leaf petiole.*—Pale green, RHS 145 B (both surfaces).

*Aspect.*—Petioles are horizontally directed, with the leaf blades are borne horizontally or slightly downward.

Disease/pest resistance/susceptibility: Somewhat susceptible to grey mould (Botrytis) during propagation under mist, which is typically of varieties with light green or variegated foliage.

Flowering description: Whole inflorescence with surrounding bracts: medium sized or over, rosette-like with the bracts well overlapping, almost flat to slightly funnel-shaped.

*Diameter.*—About 25–27 cm.

*Height.*—About 5 cm.

*Number of single bracts per inflorescence.*—10–11 (size over 2 cm).

*Keeping quality.*—Good quality will be maintained for about 4 weeks, no fading or turning green of the bracts.

Bracts:

*Shape.*—Ovate, with rounded bases, very weak to weak lobes, and acuminate tips.

*Size of the largest fully colored bract.*—12.5 cm long, 7.8 cm wide.

*Texture.*—Mature bracts are almost flat and moderately rugose.

*Vein color.*—Upper side hardly visible, corresponds closely to the bract color, lower side very light pale green, RHS 145 D.

*Color.*—Generally creamy-white, with hardly visible pure white margins; upper surface: RHS 150 D, near margin RHS 155 D; lower surface: RHS 150 D, margin, RHS 155 D.

*Petiole.*—10–15 mm long, upper side color cream, RHS 158 B, occasionally weakly pink infused RHS 49 D; lower side RHS 145 C.

*Cyme.*—15–20 mm in diameter, 5–10 cyathia borne in a tight cluster.

*Cyathium.*—Ovate, about 5–6 mm in diameter, medium to light green, RHS 141 D; top colorless to pale brownish-pink, RHS 159 A; total length of cyathium with female flower: about 17 mm.

*Peduncle.*—Light green, RHS 144 B, about 4–5 mm long.

*Nectar cups.*—Usually one, occasionally two per cyathium, about 5–6 mm wide, deep yellow colored, RHS 12 A, no reddish infusion.

Reproductive organs:

*Stamens.*—None observed, apparently not developed.

*Pistil.*—Style and stigma cream, RHS 158 B, stigma trifurcate, 6-lobed.

*Ovaries.*—Light to medium green, RHS 143 B, initially obovate, later triangular, diameter 5 mm, 6 mm long, 3 ovules.

*Fruit/seed set.*—No seed set observed.

I claim:

1. A new and distinct Poinsettia plant named 'Fiswhite Silver' as illustrated and described herein.

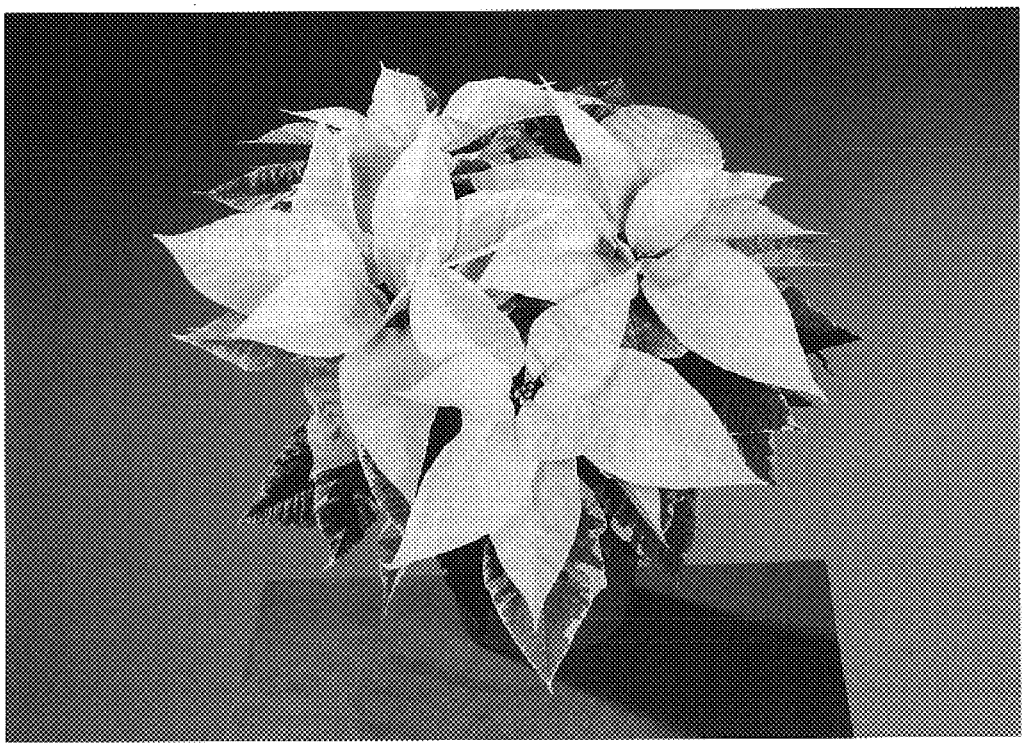

* * * * *